(12) United States Patent
Tao et al.

(10) Patent No.: US 6,838,193 B2
(45) Date of Patent: Jan. 4, 2005

(54) ORGANIC LIGHT-EMITTING DIODE

(75) Inventors: Yu-Tai Tao, Taipei (TW); Chung-Wen Ko, Taipei (TW); Chang-Hao Chuen, Taipei (TW); Jing-Wen Peng, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/294,848

(22) Filed: Nov. 14, 2002

(65) Prior Publication Data
US 2003/0186082 A1 Oct. 2, 2003

Related U.S. Application Data
(60) Provisional application No. 60/335,819, filed on Nov. 14, 2001.

(51) Int. Cl.$^7$ .................. H05B 33/14; C07D 471/14
(52) U.S. Cl. .............. 428/690; 428/917; 313/504; 313/506; 257/102; 257/103; 546/82; 548/359.5; 252/301.16
(58) Field of Search ................. 428/690, 917; 313/504, 506; 257/102, 103; 546/82; 548/359.5; 252/301.16

(56) References Cited

U.S. PATENT DOCUMENTS
5,405,709 A 4/1995 Littman et al. ............ 428/690

FOREIGN PATENT DOCUMENTS
| FR | 1320416 | * 3/1963 | |
| WO | WO 98/28296 | * 7/1998 | |
| WO | WO 98/49219 | 11/1998 | ........... C08G/73/06 |

OTHER PUBLICATIONS

Kido, Junji et al., "Multilayer White Light–Emitting Organic Electroluminescent Device", Mar. 3, 1995, Science, vol. 267, pp. 1332–1334.*
Chuen, C.H. et al., "Highly–bright white organic light–emitting diodes based on a single emission layer", Dec. 9, 2002, Applied Physics Letters, vol. 81, No. 24, pp. 4499–4501.*
Tao, Y.T. et al., "Efficient Blue Light–Emitting Diodes Based On Triarylamine–Substituted Dipyrazolopyridine Derivatives", (2002), vol. 14, pp. 4256–4261.*
Tameev, et al. "A Study of Electron Transport In Bispyrazolopyridine Derivatives", Mol. Cryst. Liq. Cryst., (2002), vol. 384, pp. 43–48.*
Parusel et al., "Theoretical Description of Solvent Effects of Fluorescence Spectra of Bulky Charge Transfer Compound DMA–DMPP", Journal of Computational Chemistry, vol. 19, No. 14, pp. 1584–1595 (1998).*
E. Balasubramaniam et al., "Blue Light–Emitting Diodes Based on Dipyrazolopyridine Derivatives", Chem. Mater., vol. 12, No. 9, pp. 2788–2793 (2000).

Andrzej Danel et al., "Electroluminescence from novel pyrazole–based polymer systems", J. Mater. Chem., vol. 9, pp. 339–342 (1999).
R.S. Deshpande et al., "White–light–emitting organic electroluminescent devices based on interlayer sequential energy transfer", Applied Physics Letters, vol. 75, No. 7, pp. 888–890 (Aug. 16, 1999).
Z. He et al., "Blue electroluminescence of novel pyrazoloquinoline and bispyrazolopyridine derivatives in doped polymer matrices", J. Mater. Chem., vol. 7, No. 12, pp. 2323–2325 (1997).
R.H. Jordan et al., "White organic electroluminescence devices", Appl. Phys. Lett., vol. 68, No. 9, pp. 1192–1194 (Feb. 26, 1996).
Frank Steuber et al., "White Light Emission from Organic LEDs Utilizing Spiro Compounds with High–Temperature Stability", Advanced Materials, vol. 12, No. 2, pp. 130–133 (2000).
Z.Y. Xie et al., "White light emission induced by confinement in organic multiheterostructures", Applied Physics Letters, vol. 74, No. 5, pp. 641–643 (Feb. 1, 1999).

* cited by examiner

Primary Examiner—Dawn Garrett
(74) Attorney, Agent, or Firm—Fish & Richardson P.C.

(57) ABSTRACT

This invention features a dipyrazolo-pyridine compound of formula (I):

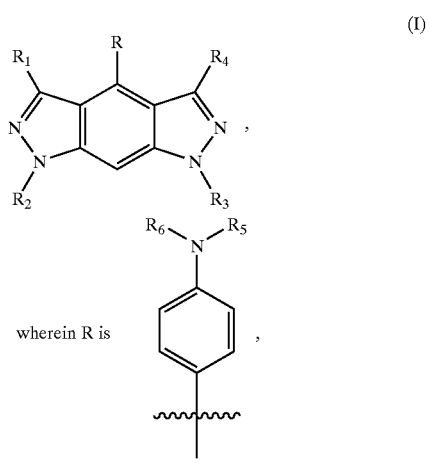

each of $R_1$, $R_2$, $R_3$, and $R_4$, independently, is H, alkyl, alkenyl, cycloalkyl, aryl, or heteroaryl; and each of $R_5$ and $R_6$, independently, is aryl or heteroaryl, or $R_5$ and $R_6$, together with the N atom they are attached to, are heteroaryl. The dipyrazolo-pyridine compound can be used in an electro-luminescence device.

56 Claims, No Drawings

ORGANIC LIGHT-EMITTING DIODE

RELATED APPLICATION

This application claims priority to U.S. Provisional Application Ser. No. 60/335,819, filed Nov. 14, 2001, the contents of which are incorporated herein by reference.

BACKGROUND

Organic light emitting diodes (OLEDs) are useful in a wide range of lighting applications, as well as high and low resolution display devices. An organic electro-luminescent device that emits white light from current-conducing organic layers is of particular interest. The white light can be obtained by co-evaporating three luminescent materials for red (R), green (G) and blue (B) luminescence to form a luminescent layer on a substrate, thereby combining the three luminescent colors to produce white luminescence. See, e.g., Tasch et al. (1997) *Appl. Phys. Lett.* 71: 2883; and Kido et al. (1994) *Appl. Phys. Lett.* 64: 815. It also can be obtained by depositing separately on the same plane of a substrate three luminescent materials for R, G and B luminescence to form luminescent layers with a pattern of the three materials, thereby producing white luminescence on the basis of simultaneous luminescence of R, G, and B. See, e.g., Kido et al. (1995) *Science* 267 1332; and Deshpande et al. (1999) *Appl. Phys. Lett.* 75, 888. There is a need for a red, green, or blue light emitting material and a need for a white light emitting electro-luminescent device that can be readily fabricated.

SUMMARY

In one aspect, this invention features a dipyrazolo-pyridine compound of formula (I) with the atoms on the dipyrazolo-pyridine ring numbered:

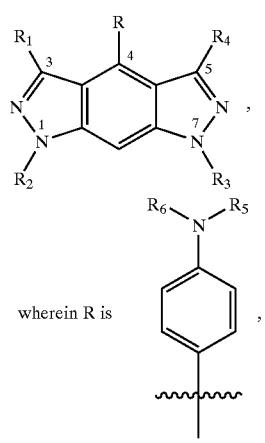

(I)

wherein R is each of $R_1$, $R_2$, $R_3$, and $R_4$, independently, is H, alkyl, alkenyl, cycloalkyl, aryl or heteroaryl; and each of $R_5$ and $R_6$, independently, is aryl or heteroaryl, or $R_5$ and $R_6$, together with the N atom they are attached to, are heteroaryl.

A subset of the compounds described above is featured by that each of $R_5$ and $R_6$, independently, is aryl (e.g., phenyl, p-tolyl, or naphthyl); or $R_5$ and $R_6$, together with the N atom they are attached to, are heteroaryl (e.g., carbazolyl).

Another subset of the compounds is featured by that each of $R_2$ and $R_3$, independently, is aryl (e.g., phenyl).

A third subset is featured by that each of $R_1$ and $R_4$, independently, is alkyl (e.g., methyl). In these compounds, each of $R_2$ and $R_3$, independently, can be aryl (e.g., phenyl); each of $R_5$ and $R_6$, independently, can be aryl (e.g., phenyl, p-tolyl, or naphthyl); or $R_5$ and $R_6$, together with the N atom they are attached to, can be heteroaryl (e.g., carbazolyl).

Exemplary compounds include 4-{4-[N-(1-naphthyl)-N-phenylaminophenyl]-1,7-diphenyl-3,5-dimethyl-1,7-dihydro-dipyrazolo[3,4-b;4'3'-e]pyridine (Compound 1), 4-[4-(di-p-tolylaminophenyl)]-1,7-diphenyl-3,5-dimethyl-1,7-dihydro-dipyrazolo[3,4-b;4'3-e]pyridine (Compound 2), 4-[4-(N,N-diphenylaminophenyl)]-1,7-diphenyl-3,5-dimethyl-1,7-dihydro-dipyrazolo[3,4-b;4'3'-e]pyridine (Compound 3), and 4-[4-(N-carbazolylphenyl)]-1,7-diphenyl-3,5-dimethyl-1,7-dihydro-dipyrazolo[3,4-b;4'3'-e]pyridine (Compound 4). The structures of these compounds are shown below:

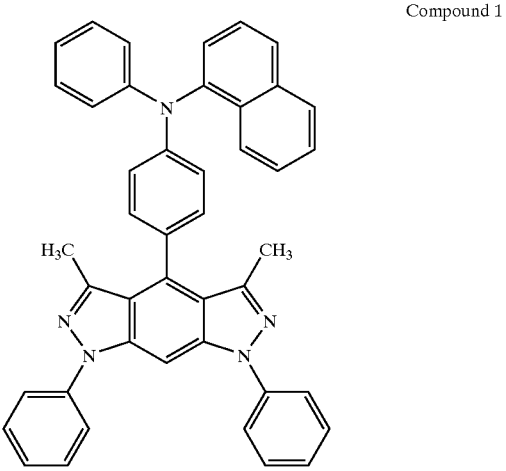

Compound 1

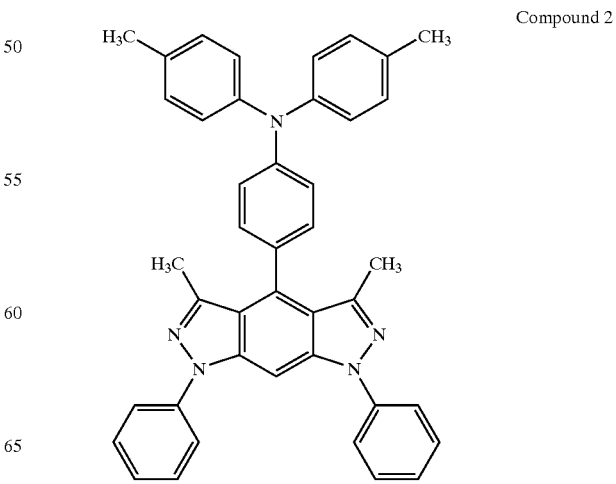

Compound 2

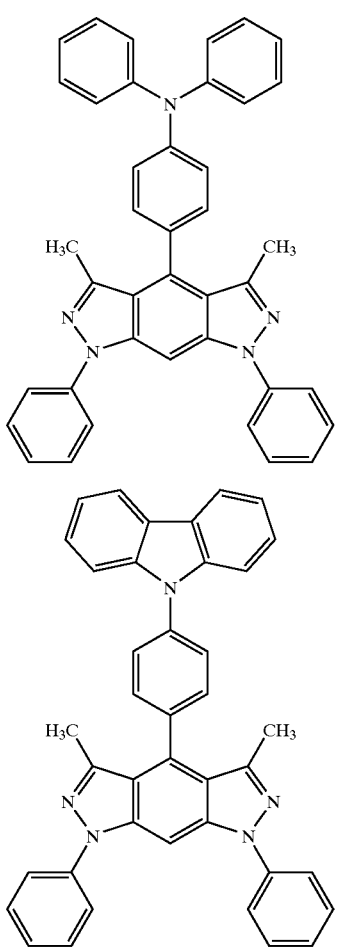

Compound 3

Compound 4

Alkyl, alkenyl, cycloalkyl, aryl, or heteroaryl mentioned above refers to both substituted and unsubstituted moieties. The term "substituted," in turn, refers to one or more substituents (which may be the same or different), each replacing a hydrogen atom. Examples of substituents include, but are not limited to, halogen, amino, alkylamino, arylamino, dialkylamino, diarylamino, alkylarylamino, hydroxyl, mercapto, cyano, nitro, $C_1$~$C_6$ alkyl, $C_1$~$C_6$ alkenyl, $C_1$~$C_6$ alkoxy, aryl, heteroaryl, cyclyl, or heterocyclyl, wherein alkyl, alkenyl, alkoxy, aryl, heteroaryl, cyclyl, and heterocyclyl are optionally substituted with $C_1$~$C_6$ alkyl, halogen, amino, alkylamino, arylamino, dialkylamino, diarylamino, alkylarylamino, hydroxyl, mercapto, cyano, or nitro.

As used herein, the term "alkyl" refers to a straight-chained or branched alkyl group containing 1 to 6 carbon atoms. Examples of alkyl groups include methyl, ethyl, n-propyl, isopropyl, tert-butyl, and n-pentyl.

The term "alkenyl" refers to a straight-chained or branched alkenyl group containing 2 to 6 carbon atoms. Examples of alkenyl groups include vinyl, allyl (2-propenyl), dimethylallyl, and butenyl.

The term "aryl" refers to a hydrocarbon ring system (monocyclic or bicyclic) having at least one aromatic ring. Examples of aryl moieties include, but are not limited to, phenyl, naphthyl, and pyrenyl.

The term "heteroaryl" refers to a hydrocarbon ring system (monocyclic or bicyclic) having at least one aromatic ring which contains at least one heteroatomn (e.g., O, N, or S) as part of the ring system. Examples of heteroaryl moieties include, but are not limited to, pyridinyl, triazolyl, tetrazolyl, pyrimidinyl, thiazolyl, indolyl, and indolizinyl.

The term "cycloalkyl" or the terms "cyclyl" and "heterocyclyl" refer to partially and fully saturated mono- or bi-cyclic rings having from 4 to 14 ring atoms. A heterocyclyl ring contains one or more heteroatoms (e.g., O, N, or S) as part of the ring. Exemplary cycloalkyl, cyclyl and heterocyclyl rings include cycylohexane, piperidine, piperazine, morpholine, thiomorpholine, and 1,4-oxazepane.

In another aspect, this invention features an electro-luminescence device. The device includes an anode layer, a hole transporting layer, a light emitting layer, an electron transporting layer, and a cathode layer. The anode layer, the hole transporting layer, the light emitting layer, the electron transporting layer, and the cathode layer are disposed in the above order. The light emitting layer includes one or more dipyrazolo-pyridinyl compounds described above.

Also within the scope of this invention is a white light emitting electro-luminescence device. The device includes an anode layer, a hole transporting layer, a light emitting layer, an electron transporting layer, and a cathode layer. The light emitting layer contains a blue light emitting layer and a red light emitting layer. Further, the anode layer, the hole transporting layer, the blue light emitting layer, the red light emitting layer, the electron transporting layer, and the cathode layer are disposed in the above order; and the blue light emitting layer includes a compound of formula (I), wherein each of $R_1$–$R_4$ and R, independently, is H, alkyl, alkenyl, cycloalkyl, aryl, or heteroaryl. A subset of the dipyrazolo-pyridinyl compounds are featured by that each of $R_1$ and $R_4$, independently, is alkyl (e.g., methyl), each of $R_2$ and $R_3$, independently, is aryl (e.g., phenyl), and R is aryl (e.g., biphenyl). Exemplary compounds include 1,7-diphenyl-4-biphenyl-3,5-dimethyl-1,7-dihydrodipyrazolo[3,4-b;4',3'-e]pyridine (Compound 5), 4-{4-[N-(1-naphthyl)-N-phenylaminophenyl]-1,7-diphenyl-3,5-dimethyl-1,7-dihydio-dipyrazolo[3,4-b4'-e]pyridine, 4-[4-(di-p-tolylaminophenyl)]-1,7-diphenyl-3,5-dimethyl-1,7-dihydro-dipyrazolo[3,4-b;4'3'-e]pyridine, and 4-[4-(N,N-diphenylaminophenyl)]-1,7-diphenyl-3,5-dimethyl-1,7-dihydro-dipyrazolo[3,4-b;4'3'-e]pyridine.

In the just described device, both the red light emitting layer and the electron transporting layer can be made of a host material, with the red light emitting layer formed by uniformly dispersing a guest component in the host material. The host material (e.g., a metal oxinoid such as tris(8-hydroxyquinolinolate)aluminum) is capable of transporting electrons, and the guest component (e.g., a fluorescent dopant such as 4-(dicyanomethylene)-2-methyl-6-(4-dimethylaminostyryl)-4H-pyran) is capable of emitting red light. The red light emitting layer may contain 0.01 to 10% by weight a guest component (e.g., 0.1%, 0.3%, 0.5%, 1%, or 5%). The percentage is based on the weight of the host material that forms the red light emitting layer. The device may further include a green light emitting layer that is interposed between the blue light emitting layer and the red light emitting layer, and is also made of the host material. It emits green light in response to red and blue light recombination. As a result, the just-described device is capable of emitting white light efficiently without a hole blocking layer. The thickness of the green light emitting layer can be in the range of 0 to 15 nm (e.g., 0 nm, 3 nm, 5 nm, or 7 nm), and the thickness of the blue or red light emitting layer can be in the range of 2 to 15 nm (e.g., 3 nm, 5 nm, 7 nm, or 10 nm).

Other features, objects, and advantages of the invention will be apparent from the description and from the claims.

DETAILED DESCRIPTION

This invention relates, in part, to dipyrazolo-pyridine compounds and their use as a light emitting material in an electro-luminescence device.

The dipyrazolo-pyridine compounds of this invention can be prepared by methods well known to a skilled person in the art (e.g., Balasubramaniam et al. (2000) *Chem. Mater.* 12: 2788; and Tao et al. (2000) *Appl. Phys. Let.* 77: 1575). For example, shown below is a scheme that depicts a synthetic route. In the scheme, $R_5$ and $R_6$ are as defined in Summary.

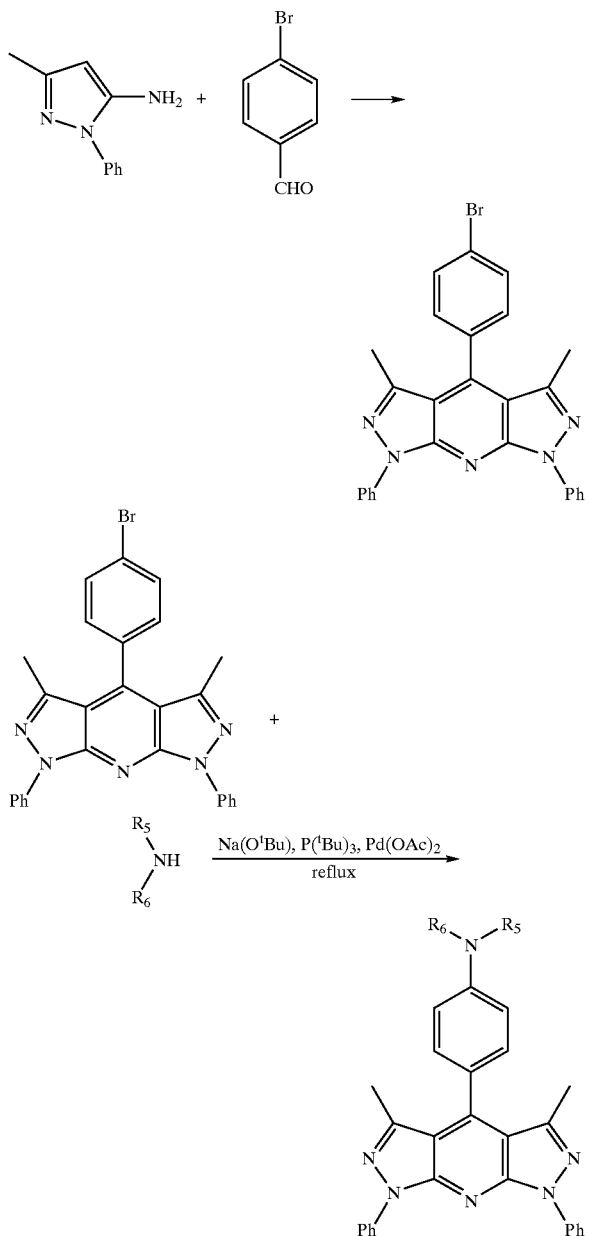

As shown in the above scheme, 5-amino-3-methyl-1-phenylpyrazole reacts with 4-bromobenz-aldehyde to obtain a dipyrazolo-pyridinyl intermediate. Other substituted pyrazole and aldehyde can also be used as starting materials (e.g., 5-amino-3-methyl-1-(4-fluorophenyl)pyrazole). The intermediate is then reacted with a di-substituted-amine in the presence of a base [e.g., Na(tBuO)], as well as catalysts [e.g., Pd(OAc)$_2$ and P(tBu)$_3$] to afford a desired dipyrazolopyridinyl product.

The chemicals used in the above-described synthetic route may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the dipyrazolo-pyridine compounds. In addition, various synthetic steps may be performed in an alternate sequence or order to give the desired dipyrazolo-pyridine compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A dipyrazolo-pyridine compound thus obtained can be further purified by flash column chromatography, high pressure liquid chromatography, recrystallization, or sublimation. It can be used as a light emitting material in an electro-luminescence device.

This invention also relates to a white light emitting electro-luminescent device that is of potential use in full-color display and can be readily fabricated. This device includes a hole transporting layer, a blue light emitting layer, a red light emitting layer, an electron transporting layer, and a pair of electrodes. The blue light emitting layer includes one or more dipyrazolo-pyridinyl compounds, e.g., 1,7-diphenyl-4-biphenyl-3,5-dimethyl-1,7-dihydrodipyrazolo[3,4-b;4',3'-e]pyridine. The just described device can emit white light by combining blue and red light emitting from the blue and red light emitting layers. Further, the device may include a green light emitting layer. The red light emitting layer can be a dopant-containing layer, and located between the blue light emitting layer and an electron transporting layer. In such an embodiment, the red light emitting layer includes not only a host material for the electron transporting layer, but also a small amount of a guest component (i.e., dopant) capable of emitting red light. The guest component can be one or more fluorescent compounds, the amount of which is usually in the range of from 0.01 to 10% by weight based on the weight of the host material. Examples of such fluorescent compounds include, but not limited to, polymethine dyes, e.g., carbocyanines and dicarbocyanines (U.S. Pat. No. 4,769,292); dicyanomethylenepyran and dicyanomethylenethiopyran dyes (U.S. Pat. No. 4,769,292); or pyrylium and thiapyrylium dyes (U.S. Pat. No. 3,615,414). A green light emitting layer, if present, is interposed between the red and blue light emitting layers, and emits green light in response to red and blue light recombination. In some embodiments, a green emitting layer is also the host of the guest component.

Typically, an electro-luminescence device can be classified into a two-layer structured device and a three-layer structured device. A two-layer structured device includes a hole transporting layer and an electron transporting layer, both of which are sandwiched between a pair of electrodes. The electron transporting layer can function as a light emitting layer, which transports electrons and emits lights (Tang et al., (1989). *J. Appl. Phys.* 65: 3610). Generally, an anode layer, a hole transporting layer, an electron transporting layer, and a cathode layer are deposited sequentially in the above order. The anode layer can be formed on a substrate, such as a glass. A three-layer structured device includes a hole transporting layer, a light emitting layer, and an electron transporting layer in the above order. The light emitting layer can be one hole transporting or one electron transporting layer. Optionally, an electro-luminescence device includes a dopant-containing layer. The blue, green, and red light emitting layers in the device described above function as a light emitting layer.

Each of the just-mentioned layers can be made of various materials, as described in, for example, U.S. Pat. No. 5,698, 740. More specifically, a substrate can be made of, e.g., glass; an anode layer can be a film of a transparent electro-conductive material, e.g., indium tin oxide (ITO), formed on the substrate; a hole transporting layer can be made of, e.g., 4,4'-bis[N-(1-naphthyl)-N-phenyl-amino]-biphenyl (NPB), formed on the anode layer; an electron transporting layer can be made of, e.g., 1,3,5-tris(N-phenyl-benzimidazol-2-yl)-benzene (TPBI), or tris(8-hydroxyquinolinolate)aluminum (AlQ), deposited on the hole transporting layer; and a cathode layer can be made of a metal film, e.g., an alloy of magnesium and silver (Mg:Ag). The fabrication of an electro-luminescence device has been described in, for example, Tang & VanSlyke (1987) *Appl. Phys. Lett.* 51: 913; Tang et al., (1989) *J. Appl. Phys.* 65: 3610, or Kido & Lizumi (1997) *Chem. Lett.* 963. More specifically, each layer may be formed by any one of film forming methods such as vacuum deposition. See U.S. Pat. No. 5,698,740. Unexpectedly, the device of this invention is capable of efficiently emitting blue light, or white light without using a hole blocking layer to control the amount of exciton formation in the hole and electron transport layers. See, e.g., Kido et al. (1995) *Science* 267: 1332; and Deshpande et al. (1999) *Appl. Phys. Lett.* 75: 888. For example, a device delineated herein includes a green emitting layer that is also the host of a guest component (i.e., dopant). To fabricate such a device, a host material is deposited first for one thickness, the guest component is coevaporated second for another thickness, and then the host material is deposited again as an electron transporting layer.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications, including patents, cited herein are hereby incorporated by reference in their entirety.

General

NMR spectra were recorded on a Bruker AC 300 spectrometer. Absorption spectra were measured on a HP 8453 spectrometer. Emission spectra were obtained from a Hitachi F-4500 fluorimeter. DSC measurements were carried out on a Perkin-Elmer DSC7 calorimeter, with a heating rate of 20° C./min under a nitrogen atmosphere. Cyclic voltammetric experiments were performed using a BAS 100B electrochemical analyzer. A three-electrode cell system with a glassy carbon, a platinum wire, and a silver wire as the working, counter and reference electrode respectively, was used. Freshly distilled, degassed dichloromethane was used as the solvent, with 0.1 M tetra-n-butylammonium hexafluorophosphate as the supporting electrolyte.

EXAMPLE 1

Synthesis of 4-{4-[N-(1-naphthyl)-N-phenylaminophenyl]-1,7-diphenyl-3,5-dimethyl-1,7-dihydro-dipyrazolo[3,4-b,4'3'-e]pyridine (Compound 1)

A mixture of 4-(4-bromophenyl)-1,7-diphenyl-3,5-dimethyl-1,7-dihydrodipyrazolo[3,4-b;4',3'-e] pyridine (1 g, 2 mmol), 1-naphthylphenylamine (444 mg, 2 mmol), sodium t-butoxide (292 mg, 3 mmol), and palladium(II) acetate (5.4 mg, 0.024 mmol) was placed in a round-bottom flask and purged with nitrogen. 40 ml of dry toluene was added to the mixture, followed by addition of tri-t-butylphosphine (0.015 ml, 0.06 mmol). The solution was brought to reflux. The reaction was monitored by TLC until the starting material was all consumed. Upon cooling to room temperature, solid precipitates appeared. A small amount of water was added and the mixture was stirred for another 30 min. The precipitates were collected and washed with water and ethyl acetate to yield crude product (1.02 g, 80%). Further purification by gradient sublimation afforded the title compound.

m.p.: 279–280° C.

$^1$H NMR ($\delta$, CDCl$_3$): 2.23 (s, 6H), 7.03–7.08 (t,1H), 7.11–7.15 (d, 2H), 7.20–7.33 (in, 8H), 7.36–7.44 (m, 2H), 7.48–7.56 (t, 6H), 7.81–7.84 (d, 1H), 7.92–7.98 (t, 2H), and 8.39–8.42 (d, 4H).

FAB mass (m/z): 632(M$^+$).

Anal calcd (%) for C$_{43}$H$_{32}$N: C, 81.62; H, 5.10; N, 13.28; Found (%): C, 81.37; H, 4.96; N, 13.30.

EXAMPLE 2

Synthesis of 4-[4-(di-n-tolylaminophenyl)]-1,7-diphenyl-3,5-dimethyl-1,7-dihydro-dipyrazolo[3,4-b:4'3'-e]pyridine (Compound 2)

Compound 2 was prepared in the same manner as the method described in Example 1 in a yield of 72.8%.

m.p.: 246–248° C.

$^1$H NMR ($\delta$, CDCl$_3$): 2.26 (s, 6H), 2.35 (s, 6H), 7.08–7.18 (m, 10H), 7.25–7.30 (t, 4H), 7.51–7.56 (t, 4H), and 8.40–8.43 (d, 4H).

FAB mass (m/z): 610 (M$^+$).

Anal calcd (%) for C$_{41}$H$_{34}$N$_6$: C, 80.63; H, 5.61; N, 13.76; Found (%): C, 80.73; H, 5.55; N, 13.80.

EXAMPLE 3

Synthesis of 4-[4-(N,N-diphenylaminophenyl)]-1,7-diphenyl-3,5-dimethyl-1,7-dihydro-dipyrazolo[3,4-b;4'3'-e]pyridine (Compound 3)

Compound 3 was prepared in the same manner as the method described in Example 1 in a yield of 73.4%.

m.p.: 247–248° C.

$^1$H NMR ($\delta$, CDCl$_3$): 2.26 (s, 6H), 7.11–7.14 (t, 2H), 7.18–7.37 (m, 14H), 7.50–7.56 (t, 4H), 8.39–8.43 (d, 4H).

FAB mass (m/z): 582 (M$^+$).

Anal calcd (%) for C$_{30}$H$_{30}$N$_6$: C, 80.39; H, 5.19; N, 14.42; Found (%): C, 80.43; H. 5.18; N, 14.7.

EXAMPLE 4

Synthesis of 4-[4-(N-carbazolylphenyl)]-1,7-diphenyl-3,5-dimethyl-1,7-(dihydro-dipyrazolo[3,4-b:4'3'-e]pyridine (Compound 4)

Compound 4 was prepared in the same manner as the method described in Example 1 in a yield of 81.1%.

m.p.: 311–313° C.

$^1$H NMR ($\delta$, CDCl$_3$): 2.27 (s, 6H), 7.27–7.37 (m, 4H), 7.48–7.49 (d, 4H), 7.52–7.57 (t, 4H), 7.72–7.82 (q, 4H), 8.17–8.20 (d, 2H), 8.42–8.45 (d, 4H).

FAB mass (m/z): 580 (M⁺).

Anal calcd (%) or $C_{39}H_{28}N_6$: C, 80.67; H, 4.86; N, 14.47; Found (%): C, 80.81; H. 4.66;N, 14.48.

TPBI was prepared from benzene-1,3,5-tricarbonyl chloride and N-phenyl-1,2-phenylenediamine, followed by dehydration. See, e.g., Shi et at. (1997) U.S. Pat. No. 5,645,948; and Chen & Shi (1998) *Coord. Chem. Rev.* 171: 161. NPB and AlQ were prepared by methods well known in the art. All charge transporting materials were subjected to gradient sublimation twice prior to use. The substrate was an ITO-coated glass with a sheer resistance of ~50 Ω/sq.

EXAMPLE 5

Fabrication of Electro-Luminescent Devices

A pre-patterned ITO substrate with an effective individual device area of 3.14 mm² was cleaned by sonication in a detergent solution for 3 min and then washed with large amount of doubly distilled water. Further sonication in an ethanol solution for 3 min was done before blowing dry with a stream of nitrogen. The ITO substrate was then treated with oxygen plasma for one minute before loaded into a vacuum chamber. Organic layers were deposited thermally at a rate of 0.1–0.3 nm/s under a pressure of ~2×10⁵ Torr in an Ulvac Cryogenic deposition system. A device was constructed with 40 nm of NPB as a hole transporting layer (HTL), 10 nm of a dipyrazolo-pyridine compound of this invention (PAP-X) as a light emitting layer and 30 nm of AlQ or TPBI as an electron transporting layer (ETL). An alloy of magnesium and silver (ca. 10:1, 50 nm) was deposited as a cathode, which was capped with 100 nm of silver. The current-voltage-luminance was measured in ambient with a Keithley 2400 Source meter and a Newport 1835C Optical meter equipped with 818ST silicon photodiode.

Thermal Properties

Compounds 1–4 were synthesized as described above. They possess high melting points (≧~250° C.). Differential scanning calorimetry (DSC) measurement showed that a glass transition temperature ($T_g$) between 87° C. and 119° C. was observed for these four compounds: Compound 3<Compound 2<Compound 1<Compound 4 (see Table 1). While Compounds 1–3 exhibited a typical crystallization phase change after heated beyond $T_g$, Compound 4 exhibited two crystallization peaks beyond $T_g$, which may be associated with two different crystal phases. See, e.g., Shirota (2000) *Mater. Chem.* 10: 1; Justin Thomas et al. (2002) *Chem. Mater.* 14: 1354; and Justin Thomas et al., (2002) *Chem. Mater.* 14:2796.

Optical Properties

UV absorption spectra of Compounds 1–4 were taken in dichloromethane ($CH_2Cl^2$). The $\lambda_{max}$ values are shown in Table 1. Same spectral pattern was observed Compounds 1–4. Strong absorption occurred at wavelength 250–450 nm one emission peak was observed in the photoluminescence (PL) spectra and the peak positions ($\lambda_{em}$) are also listed in Table 1. The quantum yields (Q.Y.) using Coumarin 1 as the reference were rather similar, in the range around 50%. The solid state PL spectra ($\lambda_{em}$) were measured for thin films of these compounds evaporated on a glass substrate. They were blue-shifted relative to the PL in $CH_2Cl_2$ solution except for Compound 4, which has the same $\lambda_{em}$. Molecular simulation (using Spartan Pro program) indicated that in Compounds 1–3, the freely rotating aryl groups approached a co-planar geometry around the nitrogen, whereas in Compound 4, the nitrogen was not planar.

Electrochemistry

Compounds 1–4 exhibited an irreversible oxidation peak at glassy carbon electrode at potentials around 1.0–1.3 eV relative to the Ag/AgCl electrode. The oxidation potentials were lower than those reported earlier (1.56 eV). See, e.g., Balasubramanian et al. (2000) *Chem. Mater.* 12: 2788; He et al. (1997) *J. Mater. Chem.* 7: 2323; and Danel et al. (I 999) *J. Mater. Chem.* 9: 339. The oxidation potentials of the four compounds are in the following order: Compound 2<Compound 1~Compound 3<Compound 4, reflecting the electron density of the aryl groups on the nitrogen atom.

The highest occupied molecular orbital (HOMO) energy level is correlated to the oxidation potential according to an equation [IP=($E_{OX}$+4.4) eV] and the lowest unoccupied molecular orbital (LUMO) energy level is obtained by subtraction of the optical band-gap from the IP (Agrawal & Jenekhe (1996) *Chem. Mater.* 8: 579; Janietz et al. (1998) *Appl. Phys. Lett.* 73: 2453). The results are listed in Table 1. Compound 4 exhibits the lowest HOMO and LUMO values and Compound 2 has the highest values.

Electroluminescence

The strong fluorescence exhibited by the PAP-X compounds both in solution and in solid state suggests that these materials are suitable candidates for fabricating a light-emitting device. A three-layer device configuration was examined., where each of the PAP-X compounds was used in the light emitting layer and NPB wvas used in tile hole transporting layer. Either AlQ or TPBI was used in the electron transporting layer.

(a). ITO/NPB/PAP-X/AlQ/Mg:Ag Devices

Devices of ITO/NPB(40 nm)/PAP-X(10 nn)/AlQ(30 nm)/Mg:Ag(50 nm) were fabricated. Bright blue or blue-green emission was observed for these devices. For the Compound 4-based device, a blue emission at 458 nm with a full width at half maximum of 76 nm was observed. This matched that of the solid film PL of this compound, suggesting dye emission as the major component in EL. For the Compound 1-based device, a much broader emission peaking at 474 nm was obtained. In the case of the Compound 3-based device, clearly two peaks at 466 nm and 502 nm were obtained in EL. Whereas for the Compound 2-based device, the emission occurred at 508 iim, shifted by 34 nm from the corresponding PL for the solid film of Compound 2. A deconvolution of the PL spectra showed that the AlQ contribution to the EL spectra increases in the following order Compound 4<Compound 1<Compound 3<Compound 2. An analysis of the energy level alignment of various layers involved in the devices indicates that the barrier for electron-crossing from AlQ to the dye layer was the lowest for Compound 4 and the highest for Compound 2, even though the barrier for hole-crossing from the dye layer to AlQ was also the lowest for Compound 4 and the highest for Compound 2.

The performance for PAP-X-based devices are summarized in Table 2. The turn-on voltages (defined as the voltage at which a luminance >1 cd/m² was observed) for PAP-X compounds were lower than ~4 V. The operating voltage (V) at a current density of 100 mA/cm² shows a substituent dependence: Compound 2<Compound 3 Compound 1<Compound 4. The brightness ranged from 900 cd/m² to 3700 cd/m² at a driving current of 100 mA/cm². The luminance efficiency ranged from 0.9 cd/A for the Compound 4-based device to 3.66 cd/m² for the Compound 1-based device. The lower external quantum efficiency (Q.E.) reflects a much unbalanced charge recombination (Khramtchenkov et al. (1996) *J. Appl. Phys.* 79: 9283). The improved quantum efficiency from Compound 4 to Compound 2 suggests that the unbalance charge recombination was less severe (thus quantum efficiency increased). Compound 4 gave the lowest external quantum efficiency and the barrier for hole-crossing at the NPB/dye interface was also the highest. The unbalance charge recombination associated with Compound 4 might imply that at the dye/AlQ interface, there were more electrons than the holes. Note that the electrons are generally considered to be the minor carrier in a standard NPB/AlQ device (Naka et el. (2000) *Syn. Met* 111–112: 33 1).

(b) ITO/NPB/PAP-X/TPBI/Mg:Ag Devices

Devices of ITO/NPB(40 nm)/PAP-X(110 nm)/TPBI(30 nm)/Mg:Ag(50 nm) devices were also fabricated. A comparison of the PL and the EL spectra shows that emissions came from the dye layer in the devices. Nevertheless, a small shoulder at around 380 im due to TPBI emission was observed for the Compound 4-based device (Tao et al. (2000) *Appl. Phys. Lett.* 77: 933). An analysis of the energy alignment revealed that the barrier for hole-leakage to TPBI layer was the lowest for the Compound 4-based device, even though the electron-crossing from TPBI layer to the dye layer was most facile. TPBI has served as a hole-blocker in many cases due to its low-lying HOMO (Tao et al. (2000) *App. Phy. Lett.* 77: 1575; and Zhilin et al. (2000) *Thin Solid Films* 363: 61). Only in the case of a dye with low-lying HOMO will there be hole-leakage into the TPBI, giving TPBI emission. This was ill contrast with the AlQ-based devices described above. The different timing for the charges arriving the interface may relate to a different electron mobility for the two electron transporting materials (Wong et al. (2001) *Chem. Phys. Lett.* 334:61). The electron mobility is higher in AlQ and the electrons reach the dye/AlQ interface faster and the electron-crossing barrier from AlQ to the dye layer determine the amount of AlQ contribution in the EL. Results show that the contribution of AlQ emission increased with increasing thickness of AlQ. Note that similar field and film thickness dependence on the electro-luminescence was observed in a bilayer polymer device and was interpreted in terms of charge carrier range. See, e.g., Jenekhe et al. (1997) *Chem. Mater.* 9: 409; and Zhanig & Jenekhe (2000) *Macromolecules* 33: 2069. In the case where TPBI as the ETL, the electron mobility is lower, the holes reached the dye/TPBI interface earlier and the barrier for hole-crossing from the dye to the TPBI layer determined the contribution of TPBI in the EL spectra.

Nearly pure blue emission was observed for Compounds 1, 3, and 4-based devices. The Commission. Internationale de l'Eclairage (CIE) x,y coordinates and other performance characteristics are listed in Table 2. Turn-on voltages lower than 4 V were observed: 3.1 V for the Compound 2-based device, ~3.3 V for the Compounds 1 and 3-based devices, and 3.8 V for the Compound 4-based device. At a driving current of 100 mA/cm$^2$, the external quantum efficiency increased from 0.84% for the Compound 4-based device to 2.76% for the Compound 1-based device. The luminance efficiency reached 2.67 cd/A for the Compound 1-based device. A maximum brightness of more than 20,000 cd/m$^2$ was obtained for two of the devices.

EXAMPLE 6

Fabrication of a White Light Emitting Electro-Luminescent Device Without a Hole Blocking Layer Previously, most of white light electro-luminescent devices integrated a hole blocking layer to control the amount of exciton formation in hole and electron transport layers. However, using the hole blocking layer decreased the efficiency of the devices, such as the luminance efficiency being moderate (maximum brightness ~2000–13000 cd/m$^2$). Several blue emitters have been used in the multi-layered white light electro-luminescent devices. See, for example, Xie et al. (1999) *Appl. Phys. Lett.* 74: 641; Strukelj et al. (1996) *J. Am. Soc. Chem.* 118: 1213; Jordan et al. (1996) *Appl. Phys. Lett.* 68: 1192; and Steuber et al. (2000) *Adv. Mater.* 12: 130. Still, the luminance efficiency was not satisfactory.

A white light emitting electro-luminescent device was fabricated as follows: 40 mm of NPB was deposited on cleaned ITO-coated glass as a hole transporting layer, which was followed by a layer of Compound 5 as a blue light emitting layer. A thin layer of AlQ was deposited as the source of green light before a layer of 4-(dicyanomethylene)-2-methyl-6-(4-dimethylaminostyryl)-4H-pyran (DCM) doped AlQ (~0.5% by weight) was deposited as a red light emitting layer. Finally a 30 nm AlQ was also used as the electron transporting layer. As described below, relative contributions of blue, green and red light emitting can be controlled by varying the thickness of each emitting layer so that the CIE coordinates can be adjusted. The CIE coordinates (0.33, 0.33) of a balanced white emission was obtained by adjusting the thickness of each emitting layer with a performance reaching a maximum brightness of 24700 cd/m$^2$ at 15 V; and a luminous efficiency of 1.97 lm/W at 6.5 V.

Fabrication of a White Light Emitting Electro-Luminescent Device Containing Various Thickness of Green Light Emitting Layer In a device configuration of ITO/NPB(40 nm)/Compound 5(5 nm)/AlQ(x nm)/AlQ:0.5% DCM(5 nm)/AlQ(30 nm)/Mg:Ag(50 nm), the thickness of the green light emitting layer (i.e., an inserted AlQ layer located between Compound 5 and the DCM-doped AlQ layers) was changed from 0 to 5 nm in fabricated devices. The electro-luminescence spectra of the devices showed a broad band covering 400–700 nm with two emission peaks at 450 nm (from Compound 5) and 575 nm (from DCM) and one valley at about 520 nm. The depth of the valley decreased with increasing thickness of the inserted AlQ layer, indicating that the emission of AlQ has increased. The results show that the thickness of the inserted AlQ layer does not affect the emission intensity of either Compound 5 or DCM. The CIE coordinates of the devices were towards blue. A higher contribution from red light was needed.

While keeping the inserted AlQ layer at 5 nm, the thickness of DCM-doped (0.5%) AlQ layer (i.e., red light emitting layer) was varied in the device configuration of ITO/NPB(40 nm)/Compound 5(5 nm)/AlQ(5 nm)/AlQ:0.5% DCM (x nm)/AlQ(30 nm)/Mg:Ag (50 nm). The electro-luminescence spectra of fabricated devices showed that DCM emission increased with increasing thickness of the DCM-doped AlQ layer. The increased DCM emission was not due to energy transfer from AlQ, and may result from the effective trapping of charges by DCM. See, for example, Tang et al. (1989) *J. Appl. Phys.* 65: 3610; and Naka et al. (1994) *Jpn. J. Appl. Phys.* 33: LI 772. Thus, by controlling the thickness of the DCM-doped AlQ layer, a match of red light contribution relative to blue light contribution was achieved. With the device configuration of ITO/NPB(40 nm)/Compound 5(5 nm)/AlQ(5 nm)/AlQ:0.5% DCM(5 nm)/AlQ(30 nm)/Mg:Ag, a white light emission was obtained and the maximum brightness and luminous efficiency were 20830 cd/m$^2$ at 15 V and 1.38 lm/W at 7 V, respectively. However, the CIE coordinates appeared to shift with the applied voltage. The CIE coordinates of (0.35, 0.34), (0.33, 0.34), (0.32, 0.33), and (0.30, 0.32) were obtained at 6, 8, 10, and 12 V, respectively, indicating an increasing contribution of Compound 5 at increasing voltage.

Further tuning of color with varying thickness of the Compound 5 layer and the DCM-doped AlQ layers with a 3 nm inserted AlQ layer was carried out. A higher blue emission from a thicker Compound 5 layer was balanced with higher red emission from a thicker DCM-doped AlQ layer. The best result was obtained with a device configuration of ITO/NPB(40 nm)/Compound 5(7 nm)/AlQ(3 nm)/AlQ: DCM(0.5%, 7 nm)/AlQ(30 nm)/Mg:Ag(50 nm). The blue and the red emission peaks were nearly of the same intensity and, more importantly, the chromaticity was rather independent of the applied voltage. The CIE coordinates changed from (0.35, 0.34) to (0.34, 0.35) when applied voltages were from 6 to 12 V. The chromaticity values are very close to the absolute white (0.33, 0.33). Unexpectedly, the maximum brightness reached 24700 cd/m² at 15 V. A maximum quantum efficiency of 1.93% was obtained at 7.0 V. When the applied voltage was at 6.5 V, a current density of 7.7 mA/cm² and the luminous efficiency of 1.97 lm/W and a brightness >300 cd/m² were obtained respectively. The key to the high brightness of the white emission in the just-described devices was the incorporation of the bright blue light emitter, Compound 5, and the exclusion of a hole-blocking layer.

In summary, a very bright white-emission organic light-emitting diode was obtained based on a rather simple multi-heterostructure. A bright blue emitter, Compound 5, was used as a blue light emitting layer. A DCM-doped AlQ layer was used as a red light emitting layer. A thin layer of AlQ was inserted between the blue and the red emission layer for green emission. After tuning the thickness of different emitting layers, the bright white light was obtained in the device of NPB(40 nm)/Compound 5(7 nm)/AlQ(3 nm)/AlQ:0.5% DCM(7 nm)/AlQ(30 nm)/Mg:Ag(50 nm). The performance characteristics are among the highest reported by literatures. The device also has the advantage of a stable white color as a function of applied voltage.

TABLE 1

Absorption, emission and electrochemical data of PAP-X

| Compound | MW | $\lambda_{max}$, nm (CH$_2$Cl$_2$) | $\lambda_{em}$, nm (CH$_2$Cl$_2$) | $\lambda_{em}$, nm (solid film) | $T_g$, °C. | Q.Y., % | HOMO/ LUMO, eV | Band gap, eV |
|---|---|---|---|---|---|---|---|---|
| 1 | 632.75 | 261, 280 333, 365 | 490 | 460 | 102 | 53 | 5.60/2.72 | 2.88 |
| 2 | 610.75 | 260, 280 327, 373 | 520 | 474 | 97 | 42 | 5.44/2.61 | 2.83 |
| 3 | 582.70 | 260, 280 330, 361 | 494 | 458 | 87 | 52 | 5.59/2.73 | 2.86 |
| 4 | 580.67 | 259, 280 329, 377 | 454 | 454 | 119 | 51 | 5.97/3.00 | 2.97 |

TABLE 2

Performances of various PAP-X-based devices

| | | At 100 mA/cm² | | | | | | | |
|---|---|---|---|---|---|---|---|---|---|
| Devices structure | Turn-on Voltage[a] (V) | V | Brightness cd/m² | Q.E. | Luminescence Efficiency cd/A | Power Efficiency lm/W | $\lambda_{em}$ | C.I.E. | Max. brightness | Max. Q.E. (%) |
| NPB/Compound 4/AlQ | 3.7 | 7.34 | 928 | 0.65 | 0.93 | 0.40 | 458 | (0.17,0.17) | 6231 | 0.65 |
| NPB/Compound 4/TPBI | 3.8 | 6.81 | 775 | 0.84 | 0.77 | 0.36 | 450 | (0.15,011) | 5543 | 0.84 |
| NPB/Compound 3/AlQ | 3.4 | 5.82 | 2992 | 1.30 | 2.98 | 1.61 | 502 | (0.23,0.34) | 23319 | 1.32 |
| NPB/Compound 3/TPBI | 3.3 | 6.98 | 1782 | 1.87 | 1.78 | 0.80 | 456 | (0.14,0.11) | 13375 | 2.00 |
| NPB/Compound 2/AlQ | 3.3 | 5.70 | 3253 | 1.23 | 3.24 | 1.79 | 508 | (0.25,0.43) | 29702 | 1.30 |
| NPB/Compound 2/TPBI | 3.1 | 5.27 | 2335 | 1.71 | 2.33 | 1.38 | 468 | (0.14,0.18) | 21063 | 2.11 |
| NPB/Compound 1/AlQ | 3.6 | 5.95 | 3653 | 1.64 | 3.66 | 1.94 | 474 | (0.21,0.31) | 35292 | 1.70 |
| NPB/Compound 1/TPBI | 3.3 | 6.29 | 2673 | 2.76 | 2.67 | 1.34 | 456 | (0.15,0.11) | 20679 | 2.76 |

[a]Defined as the voltage at which a luminance of 1 cd/m² was obtained.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. A compound of formula (I):

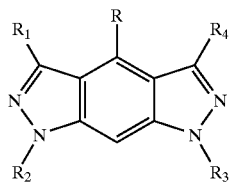

wherein
R is

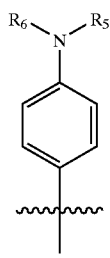

each of $R_1$, $R_2$, $R_3$, and $R_4$, independently, is H, alkyl, alkenyl, cycloalkyl, aryl, or heteroaryl; and
each of $R_5$ and $R_6$, independently, is aryl or heteroaryl, or $R_5$ and $R_6$, together with the N atom they are attached to, are heteroaryl.

2. The compound of claim 1, wherein each of $R_5$ and $R_6$, independently, is aryl.

3. The compound of claim 2, wherein each of $R_5$ and $R_6$ is phenyl.

4. The compound of claim 2, wherein each of $R_5$ and $R_6$ is p-tolyl.

5. The compound of claim 2, wherein one of $R_5$ and $R_6$ is phenyl and the other is naphthyl.

6. The compound of claim 1, wherein $R_5$ and $R_6$, together with the N atom they are attached to, are heteroaryl.

7. The compound of claim 6, wherein $R_5$ and $R_6$, together with the N atom they are attached to, are carbazolyl.

8. The compound of claim 1, wherein each of $R_2$ and $R_3$, independently, is aryl.

9. The compound of claim 8, wherein each of $R_2$ and $R_3$ is phenyl.

10. The compound of claim 1, wherein each of $R_1$ and $R_4$, independently, is alkyl.

11. The compound of claim 10, wherein each of $R_1$ and $R_4$ is methyl.

12. The compound of claim 11, wherein each of $R_2$ and $R_3$, independently, is aryl.

13. The compound of claim 12, wherein each of $R_2$ and $R_3$ is phenyl.

14. The compound of claim 13, wherein each of $R_5$ and $R_6$, independently, is aryl.

15. The compound of claim 14, wherein each of $R_5$ and $R_6$ is phenyl.

16. The compound of claim 14, wherein each of $R_5$ and $R_6$ is p-tolyl.

17. The compound of claim 14, wherein one of $R_5$ and $R_6$ is phenyl and the other is naphthyl.

18. The compound of claim 13, wherein $R_5$ and $R_6$, together with the N atom they are attached to, are heteroaryl.

19. The compound of claim 18, wherein $R_5$ and $R_6$, together with the N atom they are attached to, are carbazolyl.

20. An electro-luminescence device, comprising:
an anode layer,
a hole transporting layer,
a light emitting layer,
an electron transporting layer, and
a cathode layer,
wherein the anode layer, the hole transporting layer, the light emitting layer, the electron transporting layer, and the cathode layer are disposed in the above order; and the light emitting layer includes a compound of formula (I):

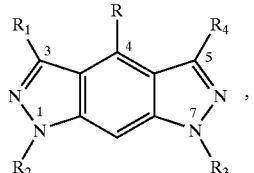

wherein R is

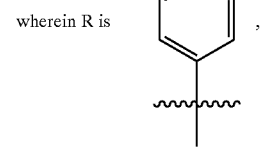

each of $R_1$, $R_2$, $R_3$, and $R_4$, independently, is H, alkyl, alkenyl, cycloalkyl, aryl, or heteroaryl; and each of $R_5$ and $R_6$, independently, is aryl or heteroaryl, or $R_5$ and $R_6$, together with the N atom they are attached to, are heteroaryl.

21. The electro-luminescence device of claim 20, wherein each of $R_5$ and $R_6$, independently, is aryl.

22. The electro-luminescence device of claim 20, wherein $R_5$ and $R_6$, together with the N atom they are attached to, are heteroaryl.

23. The electro-luminescence device of claim 20, wherein each of $R_2$ and $R_3$, independently, is aryl.

24. The electro-luminescence device of claim 20, wherein each of $R_1$ and $R_4$ independently, is alkyl.

25. The electro-luminescence device of claim 24, wherein each of $R_1$ and $R_4$ is methyl.

26. The electro-luminescence device of claim 25, wherein each of $R_2$ and $R_3$ is phenyl.

27. The electro-luminescence device of claim 26, wherein each of $R_5$ and $R_6$ is phenyl.

28. The electro-luminescence device of claim 26, wherein each of $R_5$ and $R_6$ is p-tolyl.

29. The electro-luminescence device of claim 26, wherein one of $R_5$ and $R_6$ is phenyl and the other is naphthyl.

30. The electro-luminescence device of claim 26, wherein $R_5$ and $R_6$, together with the N atom they are attached to, are carbazolyl.

31. A white light emitting electro-luminescence device, comprising:
an anode layer,
a hole transport layer,
a light emitting layer,
an electron transport layer, and
a cathode layer, wherein the light emitting layer comprises a blue light emitting layer and a red light emitting layer; the anode layer, the hole transporting layer, the blue light emitting layer, the red light emitting layer, the electron transporting layer, and the cathode layer are disposed in the above order; and the blue light emitting layer includes a compound of formula (I):

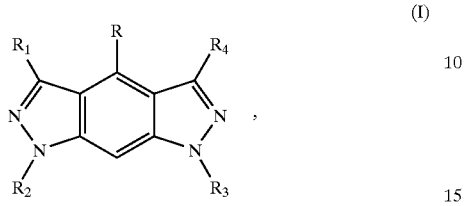

(I)

in which each of $R_1$–$R_4$, independently, is H, alkyl, alkenyl, cycloalkyl, aryl, or heteroaryl; and R is H, cycloalkyl, or

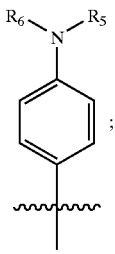

each of $R_5$ and $R_6$, independently, being aryl or heteroaryl, or $R_5$ and $R_6$, together with the N atom they are attached to, being heteroaryl.

32. The device of claim 31, wherein the red light emitting layer is made of a host material with a guest component uniformly dispersed in the host material, and the electron transporting layer is made of the same host material.

33. The device of claim 32, further comprising a green light emitting layer, wherein the green light emitting layer is interposed between the blue light emitting layer and the red light emitting layer, and is also made of the same host material.

34. The device of claim 32, wherein the host material is a metal oxinoid compound.

35. The device of claim 34, wherein the host material is aluminum trisoxine.

36. The device of claim 35, wherein the host material is tris(8-hydroxyquinolinolate)aluminum.

37. The device of claim 32, wherein the guest component is a fluorescent compound.

38. The device of claim 37, wherein the guest compound is a dicyanomethylenepyran or dicyanomethylenethiopyran dye.

39. The device of claim 38, wherein the guest compound is 4-(dicyanomethylene)-2-methyl-6-(4-dimethylaminostyryl)-4H-pyran.

40. The device of claim 32, wherein each of $R_2$ and $R_3$, independently, is aryl; and R is

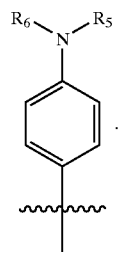

41. The device of claim 40, wherein each of $R_2$ and $R_3$ is phenyl.

42. The device of claim 40, wherein each of $R_1$ and $R_4$, independently, is alkyl.

43. The device of claim 42, wherein each of $R_1$ and $R_4$ is methyl.

44. The device of claim 43, wherein each of $R_2$ and $R_3$ is phenyl.

45. The device of claim 44, wherein R is 4-(N,N-diphenyl)aminophenyl.

46. The device of claim 44, wherein R is 4-(N,N-di-p-tolyl)aminophenyl.

47. The device of claim 44, wherein R is 4-(N-phenyl-N-naphthalen-1-yl)aminophenyl.

48. The device of claim 44, wherein the guest compound is a dicyanomethylenepyran or dicyanomethylenethiopyran dye.

49. The device of claim 48, wherein the host material is tris(8-hydroxyquinolinolate)aluminum.

50. The device of claim 49, wherein the guest compound is 4-(dicyanomethylene)-2-methyl-6-(4-dimethylaminostyryl)-4H-pyran.

51. The device of claim 33, wherein the green light emitting layer has a thickness of 3 to 15 nm.

52. The device of claim 51, wherein the blue light emitting layer has a thickness of 2 to 15 nm.

53. The device of claim 51, wherein the red light emitting layer contains 0.01 to 10% by weight the guest component.

54. The device of claim 53, wherein the red light emitting layer has a thickness of 2 to 15 nm.

55. The device of claim 54, wherein the blue light emitting layer has a thickness of 2 to 15 nm.

56. A white light emitting electro-luminescence device, comprising:
   an anode layer,
   a hole transport layer,
   a light emitting layer,
   an electron transport layer, and
   a cathode layer,
wherein the light emitting layer comprises a blue light emitting layer having a thickness of 2 to 15 nm, a green light emitting layer having a thickness of 3 to 15 nm, and a red light emitting layer; the anode layer, the hole transporting layer, the blue light emitting layer, the green light emitting layer, the red light emitting layer, the electron transporting layer, and the cathode layer are disposed in the above order; the red light emitting layer is made of a host material with a guest component uniformly dispersed in the host material; the green light emitting layer and the electron transporting layer is made of the same host material as that of the red light emitting layer; and the blue light emitting layer includes a compound of formula (I):

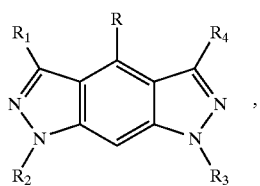
(I)
in which each of $R_1$–$R_4$, independently, is H, alkyl, alkenyl, cycloalkyl, aryl, or heteroaryl; and R is H, alkyl, alkenyl, cycloalkyl, heteroaryl, or
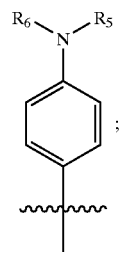
each of $R_5$ and $R_6$, independently, being aryl or heteroaryl, or $R_5$ and $R_6$, together with the N atom they are attached to, being heteroaryl.
* * * * *